(12) United States Patent
Sheppard, Jr.

(10) Patent No.: US 8,604,810 B2
(45) Date of Patent: Dec. 10, 2013

(54) MULTI-CHANNEL POTENTIOSTAT FOR BIOSENSOR ARRAYS

(75) Inventor: Norman F. Sheppard, Jr., New Ipswich, NH (US)

(73) Assignee: MicroCHIPS, Inc., Lexington, MA (US)

( * ) Notice: Subject to any disclaimer, the term of this patent is extended or adjusted under 35 U.S.C. 154(b) by 427 days.

(21) Appl. No.: 12/905,710

(22) Filed: Oct. 15, 2010

(65) Prior Publication Data

US 2011/0089957 A1 Apr. 21, 2011

Related U.S. Application Data

(60) Provisional application No. 61/252,329, filed on Oct. 16, 2009.

(51) Int. Cl.
*G01R 27/08* (2006.01)
(52) U.S. Cl.
USPC .......................................................... 324/692
(58) Field of Classification Search
None
See application file for complete search history.

(56) References Cited

U.S. PATENT DOCUMENTS

| | | | |
|---|---|---|---|
| 4,655,880 A | 4/1987 | Liu | |
| 7,226,442 B2 | 6/2007 | Sheppard, Jr. et al. | |
| 7,510,551 B2 | 3/2009 | Uhland et al. | |
| 7,842,174 B2 * | 11/2010 | Zhou et al. | 324/76.11 |
| 8,378,669 B2 * | 2/2013 | Wang et al. | 324/228 |
| 2005/0211571 A1 | 9/2005 | Schulein et al. | |
| 2005/0247559 A1 * | 11/2005 | Frey et al. | 204/403.01 |
| 2006/0057737 A1 | 3/2006 | Santini, Jr. et al. | |
| 2006/0076236 A1 | 4/2006 | Shah et al. | |
| 2007/0285099 A1 * | 12/2007 | Lorimer et al. | 324/446 |
| 2007/0299617 A1 | 12/2007 | Willis | |
| 2008/0223719 A1 | 9/2008 | Tam | |
| 2008/0249385 A1 | 10/2008 | Phan | |
| 2008/0302659 A1 | 12/2008 | Sheppard, Jr. et al. | |
| 2009/0114537 A1 | 5/2009 | Bourgerette et al. | |

(Continued)

FOREIGN PATENT DOCUMENTS

| | | | | |
|---|---|---|---|---|
| EP | 2056101 A1 | 6/2009 | | |
| JP | 2008197098 A * | 8/2008 | ............. | G01N 27/26 |

OTHER PUBLICATIONS

English translation of JP2008-197098 filed Aug. 28, 2008.*

(Continued)

*Primary Examiner* — Jermele M Hollington
(74) *Attorney, Agent, or Firm* — Sutherland Asbill & Brennan LLP

(57) ABSTRACT

Arrays of biosensors are provided along with methods for operating the arrays of biosensors. The array of biosensors may include a first reference electrode that is connected to an input of a first control amplifier; a first working electrode and a second working electrode in proximity with the first reference electrode; and a counter electrode that is connected to at least an output of the first control amplifier, where the first control amplifier is operative with the counter electrode to maintain a first specified voltage between the first working electrode and the first reference electrode, and between the second working electrode and the first reference electrode. The array of biosensors optionally may further include a second reference electrode that is connected to an input of a second control amplifier, where the second control amplifier is operative with the counter electrode to maintain a second specified voltage between the first working electrode and the second reference electrode, and between the second working electrode and the second reference electrode.

27 Claims, 9 Drawing Sheets

(56) References Cited

U.S. PATENT DOCUMENTS

2009/0305319 A1* 12/2009 Baudenbacher et al. ....... 435/29
2010/0134097 A1* 6/2010 Wang et al. ................... 324/228
2010/0149042 A1 6/2010 Utsi et al.
2010/0276734 A1* 11/2010 Josowicz et al. ............... 438/49

OTHER PUBLICATIONS

Joseph Y. Lucisano, "Micropower Potentiostat for Implantable Glucose Sensors", abstract, National Intitute of Diabetes and Digestive and Kidney Disease, 2005. <http://crisp.cit.nih.gov/crisp/CRISP_LIB.getdoc?textkey=6947848&p_grant_num=5R44D>.

William R. Heineman, "Chapter 6: Introduction to Analog Instrumentation." Laboratory Techniques in Electroanalytical Chemistry. Marcel Dekkar, Inc.,1984. 163-175.

Mohammad M. Ahmadi et al., "A Very Lpw Power CMOS Potentiostat for Bioimplantable Applications." Proceedings of the 9th International Database Engineering & Application Symposium, 2005. 6 pages.

Anonymous, "Potentiostat Architectures—Passive I/E Converters" website <http://www.consultrsr.com/resources/pstats/design2.htm>. Oct. 9, 2009, 3 pages.

International Search Report and the Written Opinion of the International Searching Authority of PCT/US2010/052860 mailed Feb. 2, 2011.

* cited by examiner

MULTI-CHANNEL POTENTIOSTAT FOR BIOSENSOR ARRAYS

RELATED APPLICATION

The present application claims priority to U.S. Provisional Application No. 61/252,329, filed on Oct. 16, 2009, and entitled "MULTI-CHANNEL POTENTIOSTAT FOR BIOSENSOR ARRAYS," which is hereby incorporated by reference in its entirety as if fully set forth herein.

BACKGROUND OF THE INVENTION

This invention relates to potentiostat circuit(s) and related circuitry used for controlling the operation of an array of biosensors or other electrochemical sensors.

For over five million Americans with insulin-dependent diabetes (IDDM) there are tremendous personal, health and economic costs associated with maintaining normoglycemia to manage diabetes. These include careful monitoring of blood glucose levels, managing of food intake and activity, calculating insulin requirements and self-treating multiple times daily, either by injection or through infusion via an insulin pump. The risks of poor glucose control include the life-threatening crises that can occur due to severe hypoglycemia, and the long-term complications that result from hyperglycemia.

The use of continuous glucose monitoring (CGM) devices has been shown to improve blood glucose control and safely reduce hypoglycemia. There are a number of commercially available CGM devices currently in use by persons with diabetes. These devices are biosensors which are inserted through the skin and measure interstitial fluid glucose in subcutaneous tissue. The biosensors are used in conjunction with a conventional potentiostat.

FIG. 1 illustrates a conventional potentiostat circuit that operates a single sensor. FIG. 1 was reproduced from M. Ahmadi and G. Jullien, "A Very Low Power CMOS Potentiostat for Bioimplantable Applications," Proc. 9th Intl. Database Engineering and Application Symposium (IDEAS '05), IEEE Computer Society, 2005. As shown in FIG. 1, the potentiostat circuit operates an electrochemical sensor ("Sensor Cell") having three electrodes—(1) a working electrode (WE), (2) a reference electrode (RE), and (3) an auxiliary or counter electrode (CE). The potentiostat circuit of FIG. 1 has two basic functions. The first function is to maintain a specified ($V_{bias}$) potential between the working electrode and the reference electrode. The second function is to measure the working electrode current, which is sunk by the auxiliary electrode. The working electrode current is converted to a voltage using a transimpedance amplifier with feedback resistor $R_F$.

Still referring to FIG. 1, the working electrode is maintained at a virtual circuit ground by way of the transimpedance amplifier. A control loop is established by comparing the reference electrode potential against a set point, $V_{bias}$, which is referenced to ground. The loop control amplifier drives the counter electrode to maintain the working electrode-to-reference electrode potential difference, $V_{cell}$, equal to $V_{bias}$.

FIG. 2 illustrates another conventional potentiostat that operates a single sensor in the form of an electrochemical cell. In particular, FIG. 2 shows an equivalent circuit for the electrochemical cell. In FIG. 2, the reference electrode is directly connected to the inverting input of the control amplifier, the set point voltage is applied to the noninverting input, and the auxiliary electrode is placed at its output. $R_r$ is the reference electrode impedance, $R_C$ is the compensated resistance, $R_u$ is the uncompensated resistance. As in FIG. 1, the working electrode is maintained at virtual circuit ground by feedback around the transimpedance amplifier. The output of this amplifier, $E_0$, is directly proportional to the working electrode current, i, and is equal to the product of the current and the current-measuring resistor Rm, $E_0 = -i*R_m$. However, unlike FIG. 1, the cell voltage $V_{cell}$ (working to reference electrode) is not equal to the set point voltage, $V_{bias}$. Instead, in FIG. 2, the cell voltage is the negative of the input voltage—that is, $V_{cell} = -E_i$. FIG. 2 has been reproduced from FIG. 6.7(b) of Kissinger, Lab Techniques in Electroanalytical Chemistry, Marcel Dekker Inc. 1984.

FIG. 3 illustrates another conventional potentiostat that operates a single sensor. In FIG. 3, the current measurement circuitry (I/E converter) is not part of the potential control loop since it is not required to maintain the working electrode (Wrk) at a specified potential. The sensor current is measured by inserting a sense resistor between the working electrode and the potentiostat's circuit ground. Both inputs of the I/E converter must be at high impedance if small currents are to be measured across the sense resistor Rm. Unlike FIG. 1, the working electrode is not at virtual ground. The working electrode voltage (relative to the potentiostat's ground) depends on the current flowing and will be at (i*Rm) volts. Because the working electrode is not at virtual ground, there is a differential amplifier/electrometer to measure the working to reference electrode potential difference. The arrow denoted "Wrk Sense" indicates the input from the working electrode. The differential amplifier/electrometer output is fed back to a summing junction of the control amplifier where it is summed with the desired working to reference electrode potential.

The Computer Retrieval of Information on Scientific Projects (CRISP) includes a 2005 abstract of Grant No. 5R44DK054545-03, entitled "Micropower Potentiostat for Implantable Glucose Sensors," that was issued to Glysens, Inc (hereinafter "Glysens"). In the CRISP abstract, Glysens discloses it "previously developed an implantable glucose sensor based on immobilized glucose oxidase coupled to an oxygen electrode and employed the sensor as an intravenous implant for over 100 days in dogs without recalibration." In addition, Glysens discloses "a Phase II effort to complete the development of novel micropower potentiostat instrumentation, principally for the implantable glucose sensor, but that may also find application with other implantable sensors and devices."

It would be desirable to provide an improved continuous monitoring device that contains an array of sensors that can be operated sequentially to extend the life of the device (or monitor) well beyond the operating life of an individual sensor. In addition, it would be desirable to improve the precision and reliability of the measurement by operating more than one sensor simultaneously.

SUMMARY OF THE INVENTION

Improved potentiostat circuits for the control of biosensors (or alternatively, other chemical/electrochemical sensors) are provided. The potentiostat circuits and biosensors can be useful, for example, in medical applications, such as transdermal or implantable medical devices. According to an embodiment, a continuous monitoring device includes at least two working electrodes that are operative with a single control amplifier that is configured to provide a reference electrode and an counter electrode. Each of the respective working electrodes is utilized as part of a biosensor (or alternatively, an chemical/electrochemical sensor) for detecting or measuring an analyte, in vitro or in vivo. The operability of at least two working electrodes with a single control amplifier can advantageously allow for redundancy, sequential operation, and differential or ratiometric operation between available working electrodes, thereby allowing for continuous operation of the biosensors.

According to one aspect, a system comprising a potentiostat circuit for controlling an array of biosensors is provided. In an embodiment, the system includes a first reference electrode that is electrically connected to an input of a first control amplifier; a second reference electrode that is electrically connected to an input of a second control amplifier; a first working electrode in proximity with the first reference electrode and the second reference electrode; and a counter electrode that is electrically connected to at least an output of the first control amplifier and an output of the second control amplifier, where the first control amplifier is operative with the counter electrode to maintain a first specified voltage between the first working electrode and the first reference electrode, and where the second control amplifier is operative with the counter electrode to maintain a second specified voltage between the first working electrode and the second reference electrode. The first and second specified voltages can be constant, varying, or otherwise modifiable, according to an embodiment of the invention. Likewise, the first and second voltages can be at the same or different voltages as well.

According to another aspect, a biological sensor is provided. In an embodiment, the biological sensor includes a first reference electrode that is electrically connected to an input of a first control amplifier; a second reference electrode that is electrically connected to an input of a second control amplifier; a first working electrode that is operable for sensing a biological analyte; and a counter electrode that is electrically connected to at least an output of the first control amplifier and an output of the second control amplifier, where the first control amplifier is operative with the counter electrode to maintain a first specified voltage between the first working electrode and the first reference electrode, and where the second control amplifier is operative with the counter electrode to maintain a second specified voltage between the first working electrode and the second reference electrode.

According to another aspect, a method for operating an array of biosensors is provided. In an embodiment, the method includes operating a first control amplifier that receives a first input from a first reference electrode and provides a first output to a counter electrode; enabling first current measurement circuitry for detecting at least one first current associated with a first working electrode while the first control amplifier is operative, where the counter electrode is operative with the first control amplifier to maintain a first specified voltage between the first reference electrode and the first working electrode; enabling second current measurement circuitry for detecting at least one second current associated with a second working electrode while the first control amplifier is operative, where the counter electrode is operative with the first control amplifier to maintain the first specified voltage between the first reference electrode and the second working electrode; disabling the first control amplifier; operating a second control amplifier that receives a second input from a second reference electrode and provides a second output to the counter electrode, where the first current measurement circuitry detects at least one third current associated with the first working electrode while the second control amplifier is operative, where the second current measurement circuitry detects at least one fourth current associated with the second working electrode while the second control amplifier is operative, where the counter electrode is operative with the second control amplifier to maintain a second specified voltage between the second reference electrode and the second working electrode.

According to yet another aspect, there is another method for operating an array of biosensors. In an embodiment, the method includes enabling a first sensor that comprises a first working electrode, where a first control amplifier receives an input from a first reference electrode and provides a first output to a counter electrode, wherein the first control amplifier maintains a first specified voltage between the first reference electrode and the first working electrode, where at least one first current is detected at the first sensor while the first control amplifier is operative; prior to failure of the first sensor, enabling a second sensor that comprises a second working electrode, where the counter electrode is operative with the first control amplifier to maintain the first specified voltage between the first reference electrode and the second working electrode, where at least one second current is detected at the second sensor while the first control amplifier is operative; disabling the first control amplifier; and enabling a second control amplifier that receives a second input from a second reference electrode and provides a second output to the counter electrode, wherein the counter electrode is operative with the second control amplifier to maintain a second specified voltage between the second reference electrode and the second working electrode, wherein at least one third current is detected at the first working electrode while the second control amplifier is operative, wherein at least one fourth current is detected at the second working electrode while the second control amplifier is operative.

DETAILED DESCRIPTION OF THE INVENTION

Figure 1:
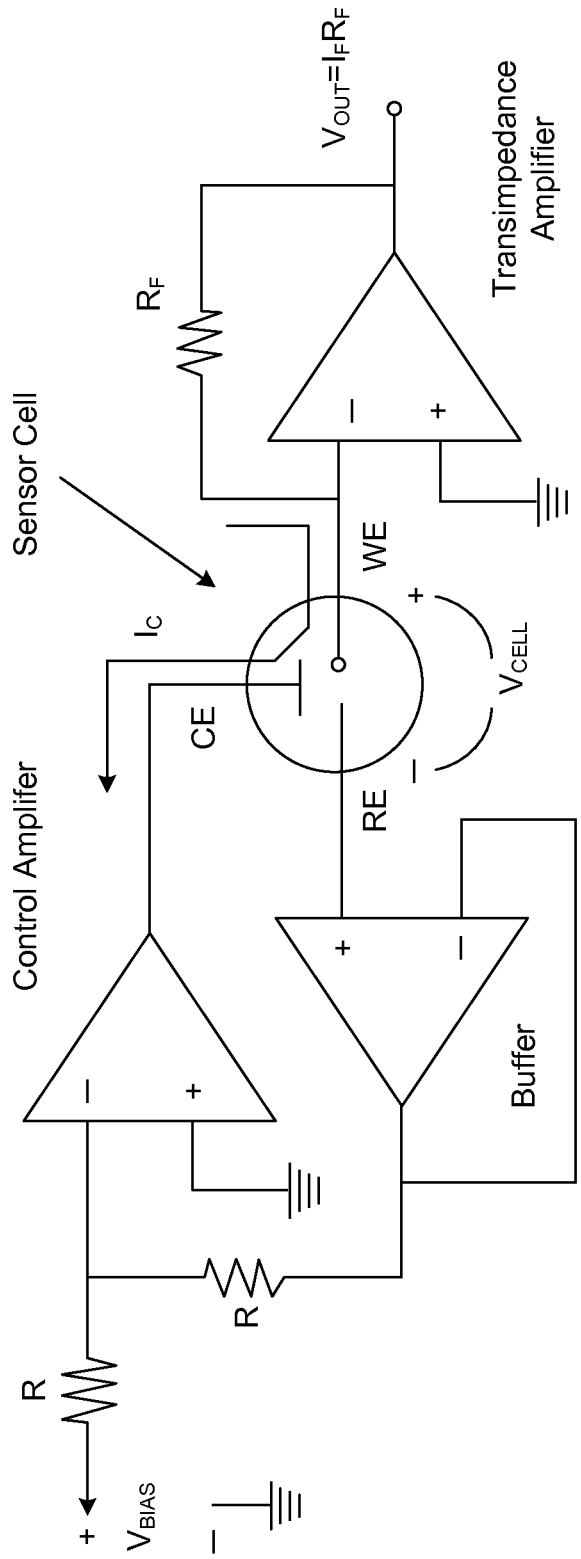
FIGS. 1-3 illustrate conventional potentiostats that control single sensor devices.
Figure 2:
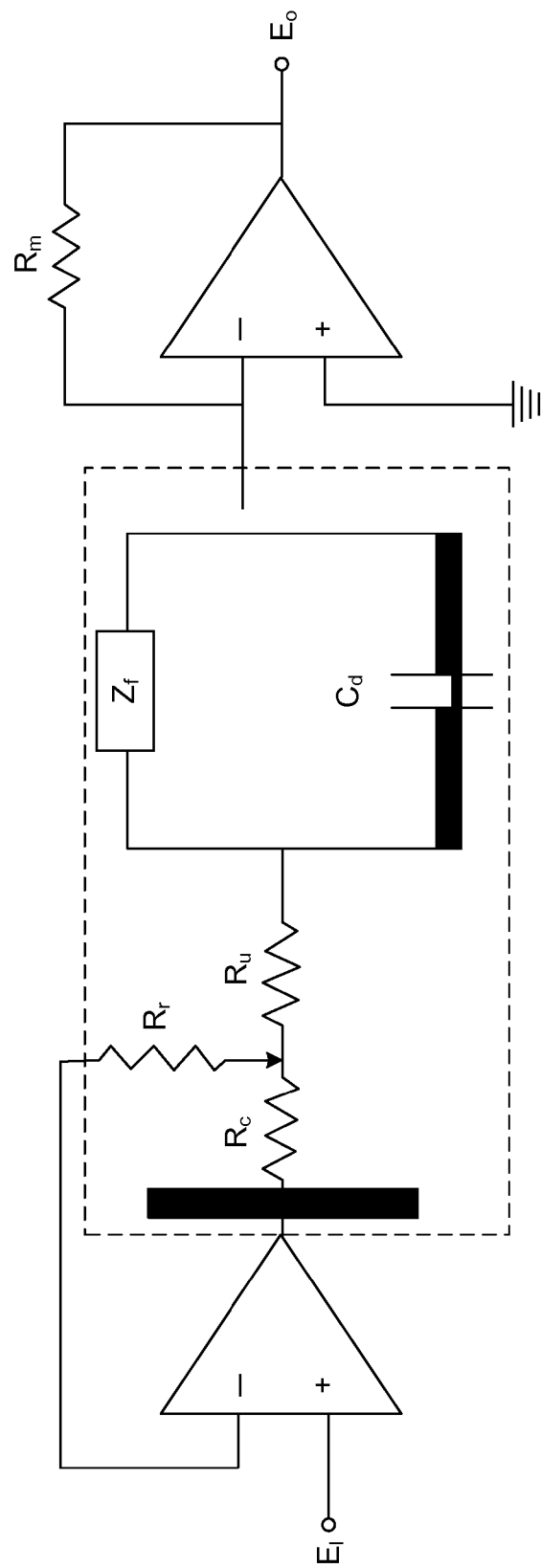
Figure 3:
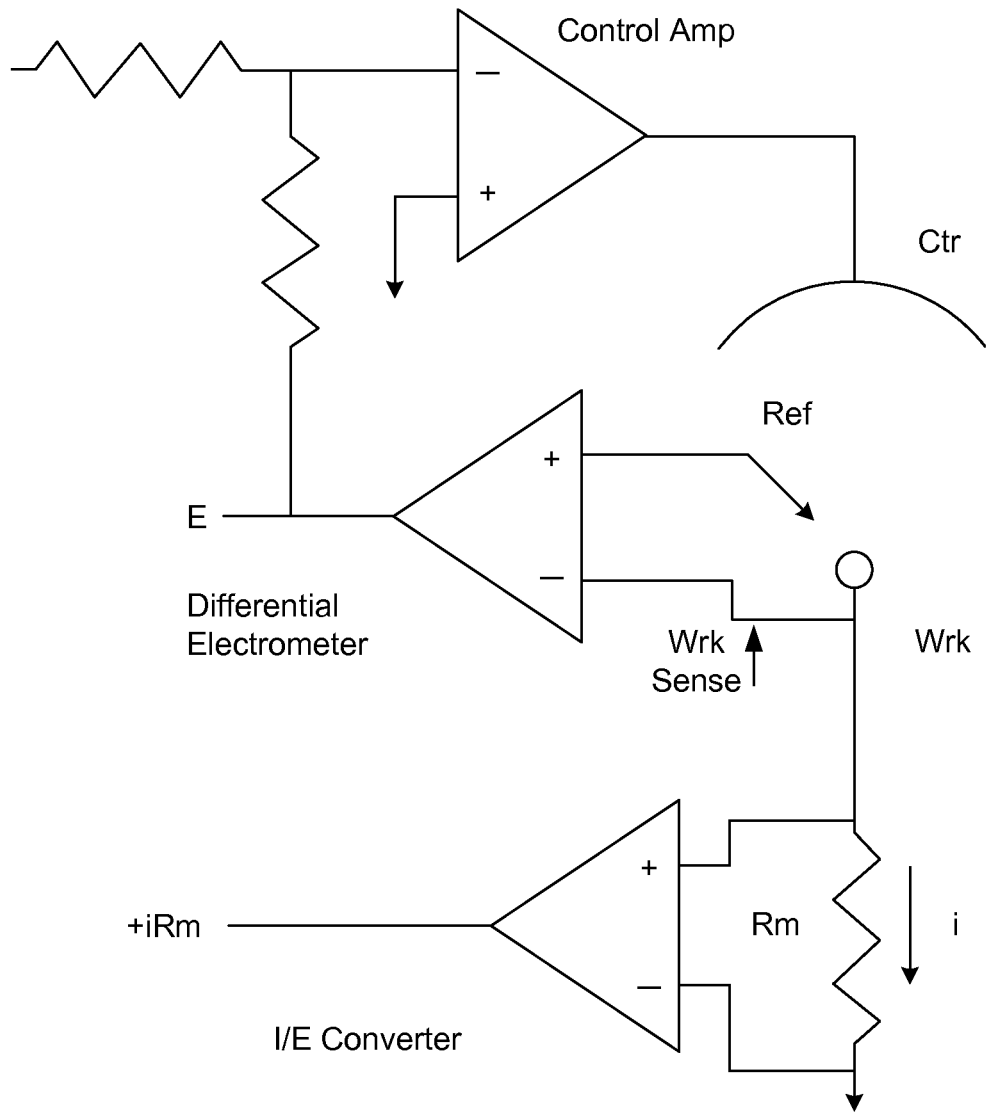

Improved potentiostat circuits for the control of biosensors (or alternatively, other chemical/electrochemical sensors) are provided. The potentiostat circuits and biosensors can be useful, for example, in medical applications, such as transdermal or implantable medical devices. According to an embodiment, a biosensor includes at least two working electrodes that are operative with a single control amplifier that is configured to provide a reference electrode and a counter electrode. Each of the respective working electrodes is utilized as part of a biosensor (or alternatively, a chemical/electrochemical sensor) for detecting or measuring an analyte, in vitro or in vivo. The operability of at least two working electrodes with a single control amplifier can advantageously allow for redundancy, controlled switching between, differential or ratiometric operation between available working electrodes, thereby allowing for continuous operation of the biosensors.

The International Union of Pure and Applied Chemistry defines an electrochemical biosensor as "a self-contained integrated device, which is capable of providing specific quantitative or semi-quantitative analytical information using a biological recognition element (biochemical receptor) which is retained in direct spatial contact with an electrochemical transduction element." See Thevenot, et al., "Electrochemical Biosensors: Recommended Definitions And Classification", *Pure Appl. Chem.*, Vol. 71, No. 12, pp. 2333-2348, 1999.

The term "biosensor" as used herein is not to be construed as being limited to sensors for medical applications. Indeed, the sensors described herein can be useful in non-medical applications. For example, the sensors may be used in diagnostic test meters for monitoring chemical parameters in non-medical samples such as water, soil, sewage, sand, air, beverage and food products, or any other suitable fluid/gel/composite sample.

According to an embodiment of the invention, an array of biosensors includes a plurality of working electrodes and one or more reference electrodes and counter electrodes. In one aspect, a monitor or device incorporating the array of biosensors includes packaging for housing electronics (e.g., potentiostat circuit) and power sources used to operate with the electrodes, as well as for protecting one or more of the electrodes, including the working electrodes, from exposure to adverse environments by enclosing them within a reservoir or an array of discrete reservoirs until needed for operation. In this way, a continuous monitor or device can be constructed by utilizing the protected electrodes in succession as their operational lifetimes are reached.

Indeed, the operational lifetime of the electrodes when used in vivo is finite due to biological tissue's foreign body response. The working electrode, which is coated with a layer of a biological recognition element (e.g., enzyme) and other layers, may experience fouling of the electrode, degradation of the enzyme layer and degradation of polymer layers. The reference electrode, which may be constructed from a reactive metal such as silver, may experience fouling, and oxidation or reduction of the electrode material leading to a drift in the reference potential. Similarly, the counter electrode may become fouled, poisoned or otherwise degraded. Accordingly, reservoirs can be used to protect one or more of the electrodes from exposure to the harmful environment of the body until they are needed.

According to an embodiment of the invention, each working, reference, and counter electrode is contained within a respective reservoir. However, in other embodiments of the invention, there are other configurations where (i) a subset of the individual electrodes making up the biosensor are contained within the same reservoir, or (ii) a subset of the electrodes making up the biosensor are not contained in a reservoir at all, e.g., located on a surface of the monitor or device outside of the reservoir. For example, a working electrode and a reference electrode can be contained in the same reservoir.

In certain embodiments, the monitor or device incorporating the array of biosensors includes a structural body which comprises at least one reservoir, or more typically an array of two or more discrete reservoirs, each reservoir having at least one opening in the structural body; one or more of the electrodes located within the reservoir; at least one discrete reservoir cap closing the at least one opening of each reservoir to isolate the electrode(s) (and associated sensor materials, if present) that are located within the reservoir and to prevent external environmental components (e.g., an analyte) outside of the reservoir from contacting the electrode therein; and activation means for rupturing or displacing the reservoir cap to permit the external environmental components (e.g., an analyte) to contact the electrode. In an embodiment, the discrete reservoir caps are in register with predefined openings in the structural body.

In certain embodiments, the structural body (which sometimes may be referred to as the "substrate"), the reservoirs, the reservoir caps, the activation means for rupturing or displacing the reservoir cap, and the methodology for packaging these various components together to form hermetically sealed reservoir devices, are described, for example, in U.S. Patent Publication No. 2008/0302659 (which describes electrochemical biosensors and arrays, including reservoirs, reservoir caps, and means for rupturing or displacing reservoir caps); U.S. Pat. No. 6,527,762 (which describes thermal means for reservoir cap rupture); U.S. Pat. No. 6,551,838; U.S. Pat. No. 6,976,982 (which describes flexible substrate/body structures); U.S. Pat. No. 6,827,250 (which describes hermetic sealed reservoir structures and sealing methods); U.S. Pat. No. 7,510,551 (which describes electrothermal ablation means for reservoir cap disintegration); U.S. Pat. No. 7,604,628 (which describes reservoir/structural body designs with multiple discrete reservoir caps closing off a single reservoir opening); U.S. Patent Application Publication No. 2006/0115323 (which describes hermetic sealed reservoir structures and compression cold weld sealing methods); and U.S. Patent Application Publication No. 2005/0096587. These patents and patent applications are incorporated herein by reference.

In an embodiment, the reservoir cap is formed of a conductive material, such as a metal film, through which an electrical current can be passed to electrothermally ablate it, as described in U.S. Pat. No. 7,455,667 to Uhland, et al. In this embodiment, the reservoir cap itself serves both as a structural barrier for isolating the contents of the reservoir from substances outside of the reservoir and as the heating element. Representative examples of suitable reservoir cap materials can include gold, copper, aluminum, silver, platinum, titanium, palladium, various alloys (e.g., Au/Si, Au/Ge, Pt/Ir, Ni/Ti, Pt/Si, SS 304, SS 316), and silicon doped with an impurity to increase electrical conductivity, as known in the art. The reservoir cap can be in the form of a multi-layer structure. An example of the multi-layer structure includes, but is not limited to, platinum deposited on titanium deposited on platinum. The reservoir cap is operably (i.e., electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (ruptured or disintegrated). The heating can be rapid and substantially instantaneous upon application of an electric current through the reservoir cap, such that no substantial heating of substances (e.g., sensor materials including synthetic polymers or biologically-derived components such as enzymes, patient tissues) adjacent to the reservoir cap occurs. In one embodiment, the reservoir cap and the conductive leads are formed of the same material, and the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed. For example, the reservoir cap and the input and output leads can be designed to provide (i) an increase in electrical current density in the reservoir cap relative to the current density in the input and output leads, upon the application of electrical current, (ii) that the material forming the reservoir cap has a different electrical resistivity, thermal diffusivity, thermal conductivity, and/or a lower melting temperature than the material forming the input and output leads, or (iii) a combination of (i) and (ii).

In another embodiment, the reservoir cap is configured as an anode and the device further includes a cathode, along with electrical circuitry, a power source, and controls for applying an electric potential between the cathode and anode in an electrically conductive fluid environment (e.g., in vivo) to cause the reservoir cap to disintegrate as described in U.S. Pat. No. 5,797,898 to Santini Jr. et al.

In still another embodiment, the reservoir cap is configured to rupture by heating using a separate resistive heating element, which is located either inside the reservoir or outside the reservoir, generally adjacent to the reservoir cap, as described for example in U.S. Pat. No. 6,527,762 to Santini Jr. et al.

Figure 4A:
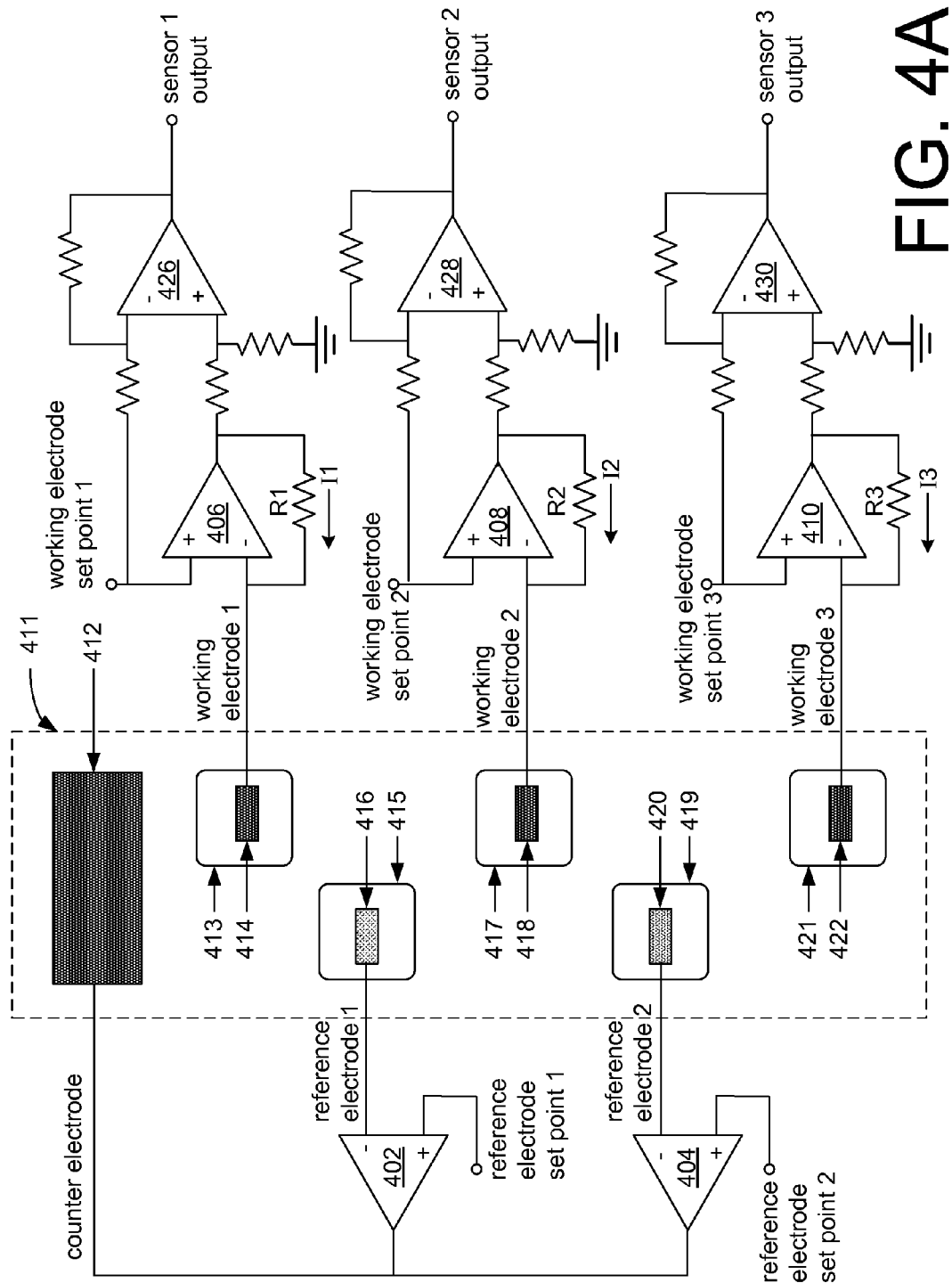
FIG. 4A illustrates a potentiostat circuit that controls an array of biosensors in which the working electrodes and reference electrodes are located in respective reservoirs.
Figure 4B:
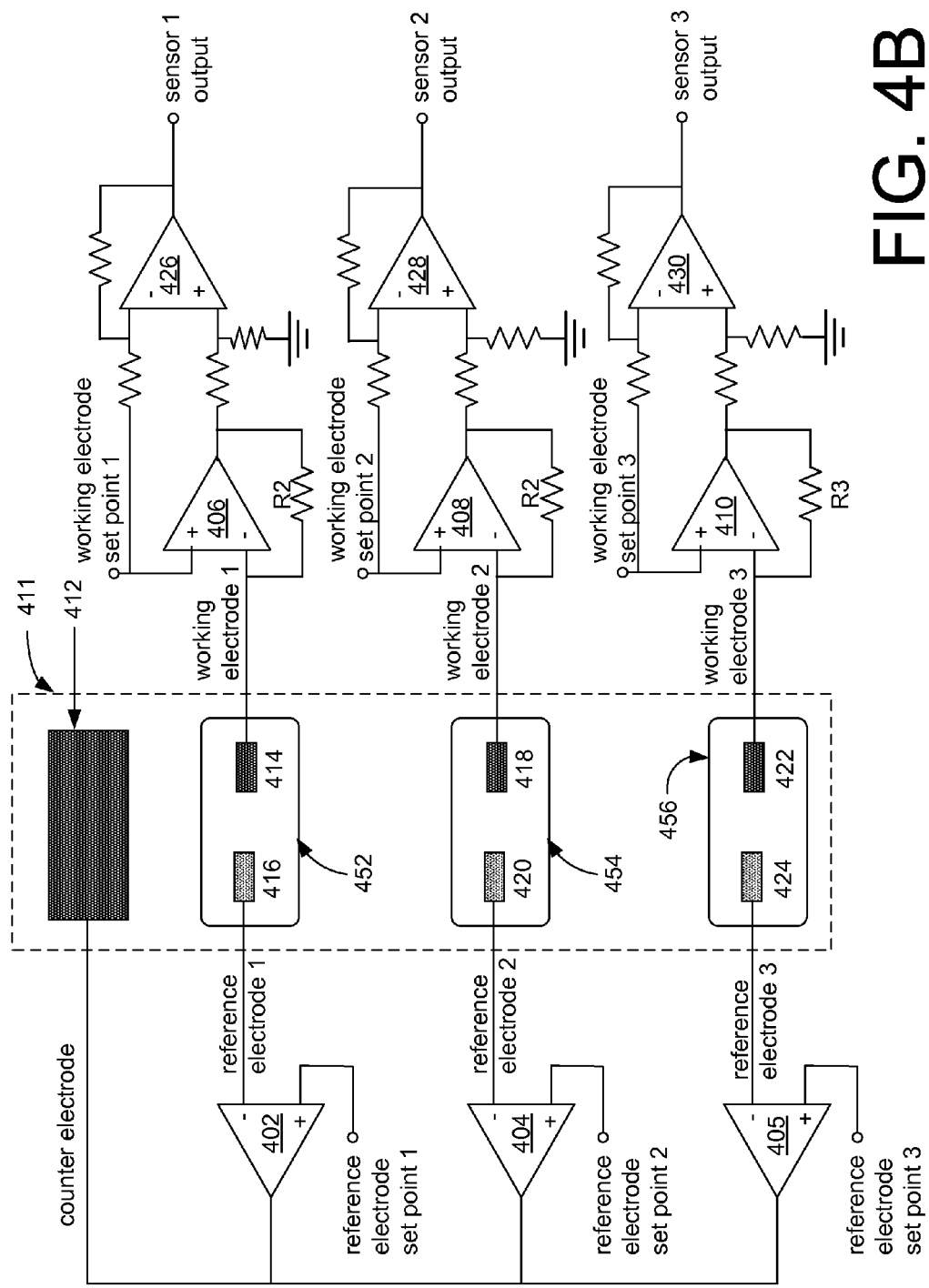
FIG. 4B illustrates a variation of FIG. 4A where pairs of working and reference electrodes are located within respective reservoirs.
Figure 4C:
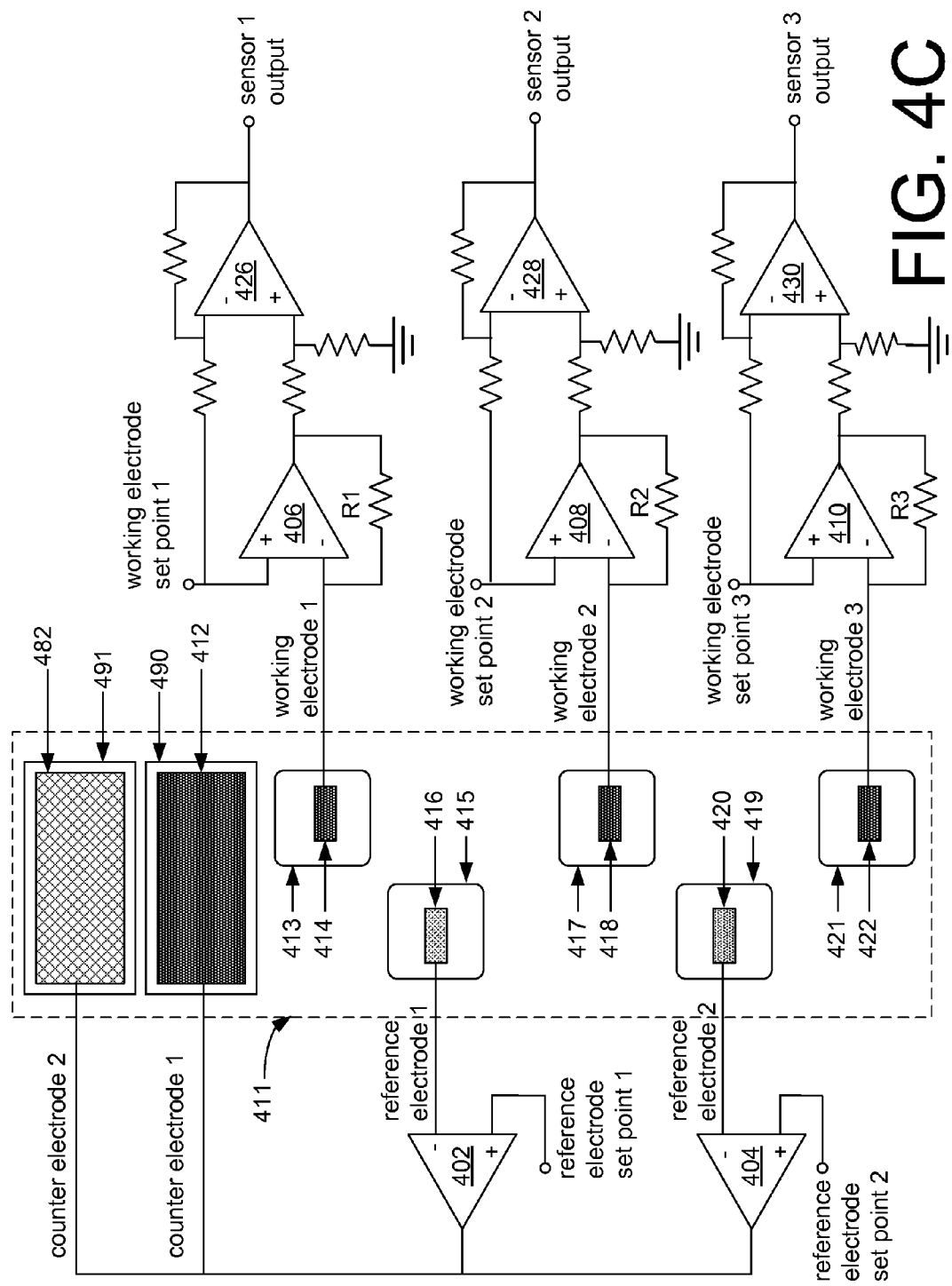
FIG. 4C illustrates another variation of FIG. 4A where multiple counter electrodes may be placed in respective reservoirs.

FIGS. 4A-4C illustrate embodiments of potentiostat circuits that control an array of biosensors. As described herein, the array of biosensors includes at least one reference electrode, at least one counter electrode, and a plurality of working electrodes.

As introduced above, the working electrodes optionally include or are coated with a biological recognition element, which can be an enzyme for which the analyte of interest is a biochemical substrate. Indeed, the biosensor can exploit the fact that many products of the reactions catalyzed by an enzyme or other biological recognition element are electroactive. For example, the working electrode can serve to provide a measure (e.g., sensor current) indicative of the concentration of a reaction product produced in the enzyme layer. In the presence of the analyte, electroactive products (e.g., hydrogen peroxide) are generated that result in current flow in the working electrode that are detected by a sensing resistor. Alternatively, in the presence of the analyte, electroactive species (e.g., oxygen) can be consumed that can result in current flow in the working electrode that are detected by a sensing resistor. Representative examples of suitable enzymes include glucose oxidase, glucose dehydrogenase, NADH oxidase, uricase, urease, creatininase, sarcosine oxidase, creatinase, creatine kinase, creatine amidohydrolase, cholesterol esterase, cholesterol oxidase, glycerol kinase, hexokinase, glycerol-3-phosphate oxidase, lactate oxidase, lactate dehydrogenase, alkaline phosphatase, alanine transaminase, aspartate transaminase, amylase, lipase, esterase, gamma-glutamyl transpeptidase, L-glutamate oxidase, pyruvate oxidase, diaphorase, bilirubin oxidase, and mixtures thereof. A working electrode can be constructed without an enzyme layer, for example if the biosensor is configured to measure oxygen or if it is used to compensate for effects that influence working electrode current independent of the analyte.

In addition to an enzyme (or other biological recognition element) layer, the sensor can include one, two, three, or more additional layers, typically based on synthetic polymers, deposited over the working electrode. The purpose of these layers are to block interfering substances, to improve the specificity, linearity, range and biocompatibility of the sensor, and in some cases, to modulate the properties (e.g., vascularity) of the sensor interface with surrounding tissue. Each layer provides one or more of these functionalities. For example, to confer linearity, a polymer layer can restrict or retard the flux of an analyte (e.g., glucose) that is allowed to contact an enzyme layer of the working electrode. To confer specificity, another polymer layer can allow the product generated by a reaction between the enzyme and the analyte to contact the working electrode while preventing other molecules from contacting the working electrode. Likewise, to confer biocompatability, another polymer layer may comprise a hydrogel to protect the working electrode from fouling when implanted in vivo.

As described herein, the sensor working electrode can be contained within a sealed reservoir in order to protect the biological recognition element (e.g., enzyme or antibody) and other sensor materials from the in vivo environment until needed, while the other electrodes, such as the reference and counter electrodes, making up the sensor's electrochemical cell are variously located inside or outside of the same or different reservoirs as the working electrode, as described herein. Indeed, the working electrode can be provided in a sealed reservoir for selective exposure (such as at the precise time the electrode is needed for a particular sensor to function) in order to protect the working electrode against (i) fouling of the outer layer of the sensor by proteins and cells which can influence transport of analyte to the enzyme layer, (ii) degradation of the enzyme by the hydrogen peroxide produced by oxidase enzymes, (iii) degradation of polymer layers, for example, the hydrolysis of ester linkages of polyurethane membranes, and (iv) degradation processes mediated by cells of the immune system (e.g., macrophages, foreign body giant cells). In addition, hermetically sealed reservoirs enable the environment (e.g., inert gas atmosphere, humidity) inside the sealed reservoir to be controlled, which can lead to a longer lifetime of the biosensor, such as a longer shelf (storage) life of the biosensor.

Similarly, the operational lifetimes of reference electrodes and counter electrodes when used in vivo can also be finite due to the body's foreign body response. The reference electrode, which may be constructed from a reactive metal such as silver, may experience fouling, and oxidation or reduction of the electrode material leading to a drift in the reference potential. Similarly, the counter electrode may become fouled or poisoned. Thus, reservoirs and associated caps or covers, as described herein, can also be utilized with can be used to protect these electrodes from exposure to the harmful environment of the body until they needed.

In one embodiment, the biosensor is a glucose biosensor based on the enzyme glucose oxidase. The glucose oxidase is coated on a working electrode of the glucose biosensor. The enzyme-catalyzed conversion of analyte (i.e., glucose) yields a reaction product (e.g., hydrogen peroxide or other products if compounds known as electron mediators are used in the sensor) that is redox active. The oxidation of this product at the working electrode produces a current that can be related back to the analyte (i.e., glucose) concentration or other analyte measurement. It will also be understood that the enzyme-catalyzed conversion of analyte (i.e., glucose) can consume one or more electroactive species (e.g., oxygen). The change in the electroactive species (e.g., oxygen) based upon the consumption can alternatively be detected as a generated current at the working electrode, and the current can be related back to the analyte (i.e., glucose) concentration or other analyte measurement. Accordingly, the working electrode can generate a current to sense a change in one or more generated electroactive products (e.g., hydrogen peroxide) or consumed electroactive species (e.g., oxygen).

As described herein, the working electrode is where the desired redox-active reaction component is oxidized or reduced, thereby yielding the sensor current in the working electrode. The reference electrode is used to sense the potential in the solution (where the working electrode is) by the control amplifier of the potentiostat circuit, which then adjusts the potential of the counter electrode as needed to establish a specified potential between the working electrode and the reference electrode. The reference electrode is in close proximity to the working electrode to reduce any resistive (IR) potential drops, which changes the working electrode potential. The counter electrode sinks or sources the working electrode current. The counter electrode typically is equal in area to or larger in area than the working electrode in order to reduce the current density and overpotential at the counter electrode.

FIG. 4A illustrates a potentiostat circuit that controls an array of biosensors in which the working electrodes and reference electrodes are located in respective reservoirs, according to an embodiment of the invention. More specifically, FIG. 4A illustrates a potentistat circuit that includes control amplifiers 402, 404 and transimpedance amplifiers 406, 406, 410. In addition, FIG. 4A illustrates a structural body 411 that include the array of biosensors. The array of biosensors comprises a plurality of working electrodes, including at least a first working electrode 414, a second working electrode 418, and a third working electrode 422, and a plurality of reference electrodes, including at least a first reference electrode 416 and a second reference electrode 420. In addition, the structural body 411 also includes a common counter electrode 412. It will be appreciated that while only a specific number of working electrodes, reference electrodes, and counter electrodes are illustrated, other embodiments may have fewer or more electrodes. For example, there may be more than two reference electrodes and/or more than three working electrodes without departing from example embodiments of the invention.

The potentiostat circuit of FIG. 4A can be operative to control an array of glucose biosensors or other type of sensors. According to this embodiment, the first working electrode 414, the second working electrode 418, and the third working electrode 422 can each be coated with a respective biological recognition element (e.g., glucose oxidase or another enzyme). As shown in FIG. 4A, the structural body 411 includes respective reservoirs for each of the respective working electrodes and reference electrodes. More particularly, working electrodes 414, 418, 422 are provided in respective reservoirs 413, 417, 421. Likewise, reference electrodes 416, 420 are provided in respective reservoirs 415, 419.

The openings of reservoirs 413, 415, 417, 419, and 421 are initially covered or sealed by at least one discrete reservoir cap to isolate the electrode(s) (and associated sensor materials, if present) and to prevent external environmental components (e.g., an analyte) outside of the reservoir from contacting the electrode therein. As described herein, an activation means is utilized to rupture or displace the reservoir cap when an operation of the associated electrode is needed.

Still referring to FIG. 4A, the counter electrode 412 is electrically connected to the outputs of a first control amplifier 402 and a second control amplifier 404. The first reference electrode 416 is electrically connected to the inverting input of the first control amplifier 402 while the second reference electrode 420 is electrically connected to the inverting input of the second control amplifier 404. The non-inverting inputs of the first and second control amplifiers 402, 404 are set according to one or more reference electrode set points (e.g., 0.5V or another voltage) during operation. The respective outputs of the first and second control amplifiers 402, 404 are electrically connected to a common counter electrode 412. During typical operation, only one of the two control amplifiers 402, 404 is powered and operative. In addition, the outputs of control amplifiers 402, 404 are measured during operation so that reference electrode set points and working electrode set points can be adjusted as necessary to keep the feedback control loop operational. If the output of the operative control amplifier 402, 404 is at the extreme limit of its range (i.e., approximately equal to the upper or lower power supply voltage), the desired potential difference between the working electrode and reference electrode may not be present.

Sensor current flow in the first working electrode 414 is detected by a first current measurement circuitry, which includes a first transimpedance amplifier 406 and a first sensing resistor R1. More specifically, the first working electrode 414 is electrically connected to the inverting input of the first transimpedance amplifier 406. The non-inverting input of the first transimpedance amplifier 406 is provided at a working electrode set point (e.g., +600 mV relative to the reference electrode set point, and can range, for example, from −700 to +700 mV depending on the type of sensor). The first sensing resistor R1, which is connected across the inverting input and the output of the first transimpedance amplifier 406, measures a current flow at the first working electrode 414. The output of the first transimpedance amplifier 406 may have a DC offset equal to the working electrode set point voltage. Thus, the output of the first transimpedance amplifier 406 may be as follows: Voltage Output 1=Working Electrode Set Point 1+(Current1*R1). The output of the first transimpedance amplifier 406 may be provided to a non-inverting input of a differential amplifier 426. The working electrode set point associated with the first transimpedance amplifier 406 may likewise be provided to an inverting input of the differential amplifier 426. Accordingly, an output of the differential amplifier 426 may produce a voltage that is proportional to the working electrode 414 current. A microcontroller can measure the output voltage of the differential amplifier 426 to determine information regarding the sensor current detected by the first working electrode 414. In an embodiment of the invention, additional signal conditioning or signal processing can be applied to output of the differential amplifier in order to facilitate measurement by the microcontroller. As an example, the output of the differential amplifier 426 can be converted from a voltage to a current that drives an external resistor (to the integrated circuit (IC) that includes at least the amplifiers of FIG. 4A), such that the voltage across the resistor can be filtered and measured by a microcontroller to determine information regarding the sensor current detected by the first working electrode 414.

Similarly, sensor current flow in the second working electrode 418 is detected by a second current measurement circuitry, which includes a second transimpedance amplifier 408 and a second sensing resistor R2. More specifically, the second working electrode 418 is electrically connected to the inverting input of the second transimpedance amplifier 408. The non-inverting input of the second transimpedance amplifier 408 is provided at a working electrode set point (e.g., +600 mV relative to the reference electrode set point). The second sensing resistor R2, which is connected across the inverting input and the output of the second transimpedance amplifier 408, measures a current flow at the second working electrode 418. The output of the second transimpedance amplifier 408 may have a DC offset equal to the working electrode set point voltage. Thus, the output of the second transimpedance amplifier 408 may be as follows: Voltage Output 2=Working Electrode Set Point 2+(Current2*R2). The output of the second transimpedance amplifier 408 may be provided to a non-inverting input of a differential amplifier 428. The working electrode set point associated with the second transimpedance amplifier 408 may likewise be provided to an inverting input of the differential amplifier 428. Accordingly, an output of the differential amplifier 428 may produce a voltage that is proportional to the working electrode 418 current. A microcontroller can measure the output voltage of the differential amplifier 428 to determine information regarding the sensor current detected by the second working electrode 418. In an embodiment of the invention, additional signal conditioning or signal processing can be applied to output of the differential amplifier in order to facilitate measurement by the microcontroller. As an example, the output of the differential amplifier 428 can be converted from a voltage to a current that drives an external resistor (to the IC that includes at least the amplifiers of FIG. 4A), such that the voltage across the resistor can be filtered and measured by a microcontroller to determine information regarding the sensor current detected by the second working electrode 418.

In addition, sensor current flow in the third working electrode 422 is detected by a third current measurement circuitry, which includes a third transimpedance amplifier 410 and a third sensing resistor R3. More specifically, the third working electrode 422 is electrically connected to the inverting input of the third transimpedance amplifier 410. The non-inverting input of the third transimpedance amplifier 410 is provided at a working electrode set point (e.g., +600 mV relative to the reference electrode set point). The third sensing resistor R3, which is connected across the inverting input and the output of the third transimpedance amplifier 410, measures a current flow at the third working electrode 422. The output of the third transimpedance amplifier 410 may have a DC offset equal to the working electrode set point voltage. Thus, the output of the first transimpedance amplifier 410 may be as follows: Voltage Output 3=Working Electrode Set Point 3+(CurrentI3*Resistor R3). The output of the first transimpedance amplifier 406 may be provided to a non-inverting input of a differential amplifier 430. The working electrode set point associated with the third transimpedance amplifier 410 may likewise be provided to an inverting input of the differential amplifier 430. Accordingly, an output of the differential amplifier 430 may produce a voltage that is proportional to the working electrode 422 current. A microcontroller can measure the output voltage of the differential amplifier 430 to determine information regarding the sensor current detected by the third working electrode 422. In an embodiment of the invention, additional signal conditioning or signal processing can be applied to output of the differential amplifier in order to facilitate measurement by the microcontroller. As an example, the output of the differential amplifier 430 can be converted from a voltage to a current that drives an external resistor (to the IC that includes at least the amplifiers of FIG. 4A), such that the voltage across the resistor can be filtered and measured by a microcontroller to determine information regarding the sensor current detected by the third working electrode 422.

Accordingly, the microcontroller associated with the potentiostat circuit can receive respective information (e.g., voltages) indicative of the respective currents at one or more of the working electrodes 414, 418, 422. The microcontroller can adjust the working electrode set points associated with transimpedance amplifiers 406, 408, 410, or other operations (e.g., turn on/turn off) of the transimpedance amplifiers 406, 408, 410. In addition, the microcontroller can receive the outputs (e.g., a voltage) from the control amplifiers 402, 404, and likewise adjust the associated reference electrode set points, or other operations (e.g., turn on/turn off) of the control amplifiers 402, 404. As the monitor or device that includes the microcontroller and potentiostat circuit can be embedded in vivo, the microcontroller can transmit the received information wirelessly via an antenna to a receiving computer, which can be a handheld device or other remote computing device within proximity to the embedded monitor or device. The receiving computer can convert the received information indicative of the detected sensor currents at one or more of the working electrodes 414, 418, 422 to a value of interest, such as a measurement associated with the analyte (e.g., glucose) being detected. As described herein, the receiving computer may be calibrated such that the information indicative of the detected sensor currents at one or more of the working electrodes 414, 418, 422 can be converted to the value of interest.

FIG. 4B illustrates a variation of FIG. 4A in which pairs of working and reference electrodes are located within respective reservoirs of the structure body 411, according to an embodiment of the invention. As shown in FIG. 4B, a first working electrode 414 and a first reference electrode 416 is provided in a reservoir 452. Likewise, a second working electrode 418 and a second reference electrode 420 are provided in a reservoir 454. Similarly, a third working electrode 422 and another reference electrode 424 is provided in a reservoir 454. It will be appreciated that the reference electrodes and working electrodes provided in the reservoirs may be aligned or staggered in various positions, according to an example embodiment of the invention. The openings of reservoirs 452, 454, and 456 are initially covered by at least one discrete reservoir cap to isolate the electrode(s) (and associated sensor materials such as enzymes or polymers, if present) and to prevent external environmental components (e.g., an analyte) outside of the reservoir from contacting the electrode therein. Accordingly, as described herein, an activation means is utilized to rupture or displace the reservoir cap when an operation of the associated electrode is needed.

The reservoirs 452, 456, 456 of FIG. 4B can be utilized where the usable life of the working electrodes and the reference electrodes are similar, according to an embodiment of the invention. On the other hand, the individual reservoirs 413, 415, 417, 419, 421 in FIG. 4A can be utilized, for example, where a reference electrode has a longer lifespan than a working electrode. Alternatively, individual reservoirs can also be utilized, for example, where the reference electrodes are short-lived and additional reference electrodes are needed.

FIG. 4C illustrates another variation of FIG. 4A in which multiple counter electrodes can also be provided. As shown in FIG. 4C, there may be at least two counter electrodes, including a first counter electrode 412 and a second counter electrode 491. The first counter electrode 412 and the second counter electrode 491 may be operative with the first control amplifier 402 and the second control amplifier 404, although during typical operation, only one counter electrode 412, 491 will be operative with a control amplifier 402, 404 at any particular time. Each of the first and second counter electrodes 412, 482 may be provided in respective reservoirs 490, 491. The openings of reservoirs 490, 491 are initially covered by at least one discrete reservoir cap to isolate the counter electrodes 412, 482 and to prevent external environmental components (e.g., proteins, cells) outside of the reservoir from contacting the electrode therein. Accordingly, as described herein, an activation means is utilized to rupture or displace the reservoir cap when an operation of the associated electrode is needed. It will be appreciated that the reservoirs 490, 491 may be utilized where the operation lifetimes of any one counter electrode 412, 491 may not be sufficient for sequential operation of the reference electrodes 416, 420 and the working electrodes 414, 418, 422.

An illustrative operation of the potentiostat circuit for controlling the array of biosensors of FIG. 4A will now be discussed with reference to the flow diagram of FIG. 5. One or more of the blocks or steps in FIG. 5 may be performed by a microcontroller or processing device (e.g., processor, application specific integrated circuit (ASIC), state machine, etc.) in communication with or in control of one or more components of the potentiostat circuit, including one or more control amplifiers, current measurement circuitry (or components thereof, including the respective transimpedance amplifiers and/or differential amplifiers), and the like.

Figure 5:
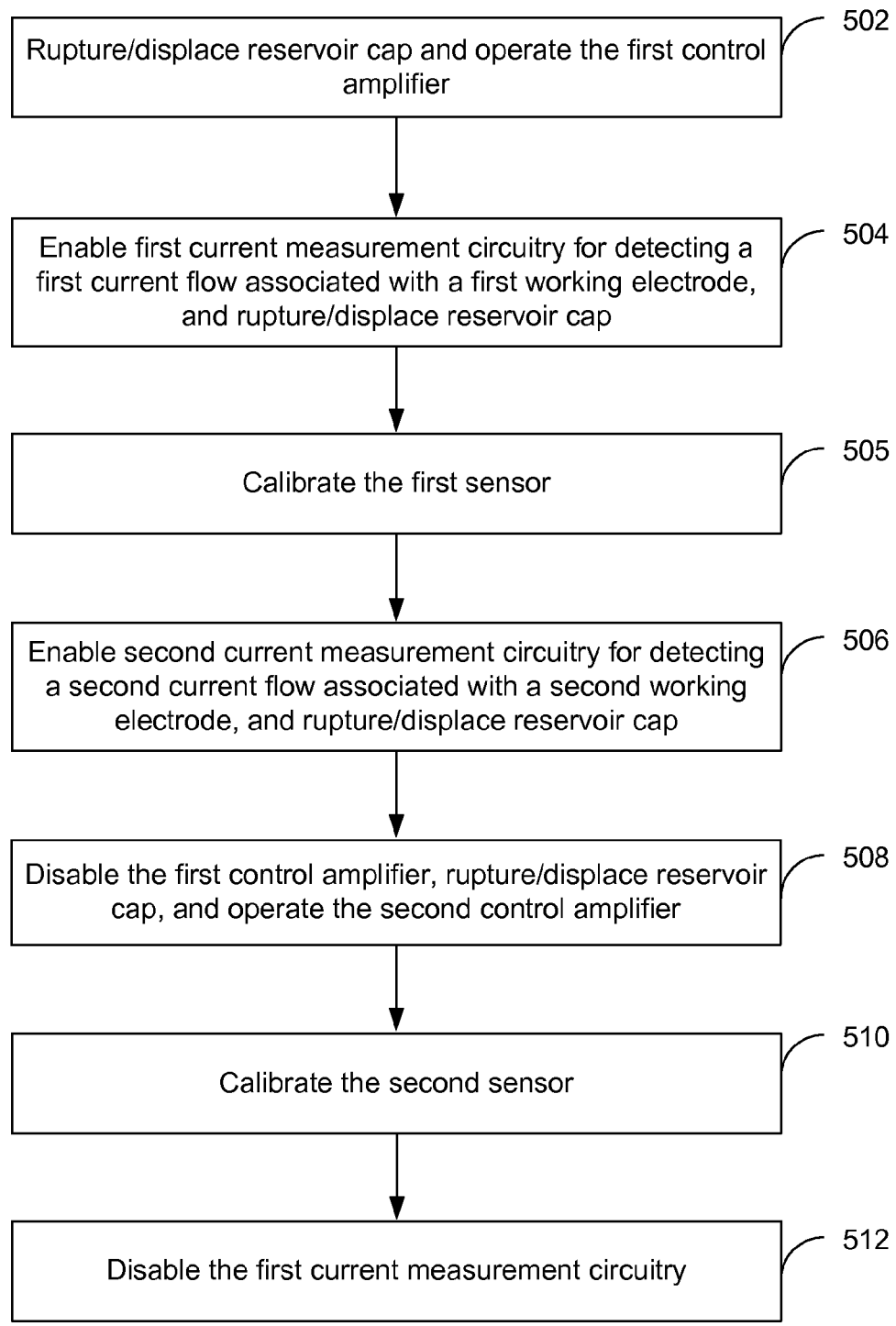
FIG. 5 provides a flow diagram illustrating an operation of a potentiostat circuit for controlling an array of biosensors, according to an embodiment of the invention.

Referring now to FIGS. 4A and 5, in block 502, a microcontroller or processing device directs the rupturing or displacement of the reservoir cap for reservoir 415 to allow external environmental components to contact the first reference electrode 416. The microcontroller or processing device then sets the first control amplifier 402 to an operative state. For example, the first control amplifier 402 is set to an operative state by providing a biasing voltage or other power to the control amplifier 402. Likewise, a reference electrode set point (e.g., 0.5V) is provided at the non-inverting input of the first control amplifier 402.

In block 504, the microcontroller or processing device enables the first current measurement circuitry. According to an embodiment of the invention, the first current measurement circuitry is enabled by providing a biasing voltage or other power to the first transimpedance amplifier 406. Likewise, a working electrode set point (e.g., +600 mV relative to the reference electrode set point) is provided at the non-inverting input of the first transimpedance amplifier 406. In addition, in block 504, the microcontroller or processing device ruptures or displaces the reservoir cap for reservoir 413 to allow external environmental components (e.g., an analyte) to contact the first working electrode 414. Since the first working electrode 414 is coated with a biological recognition element, an electroactive product is generated near the first working electrode 414 based upon the presence of the appropriate analyte. The presence of the electroactive product near the first working electrode 414 results in a first sensor current being detected by the first current measurement circuitry (e.g., transimpedance amplifier 406 and sensing resistor R1) and provided at the output of the first transimpedance amplifier 406. The output of the first transimpedance amplifier 406 may be provided to the differential amplifier 426, which may provide information associated with the detected sensor current at the first working electrode 414 to the microcontroller or processing device. It will be appreciated that the first transimpedance amplifier 406 and the first working electrode 414 may be enabled prior to rupturing or displacing the reservoir cap for reservoir 413 in order to verify that the reservoir 413 has remained sealed. For example, no current or a minimal current should be detected by the microcontroller or the processing device for the working electrode 414 if the reservoir 413 is sealed or if the seal has not been compromised.

Figure 6:
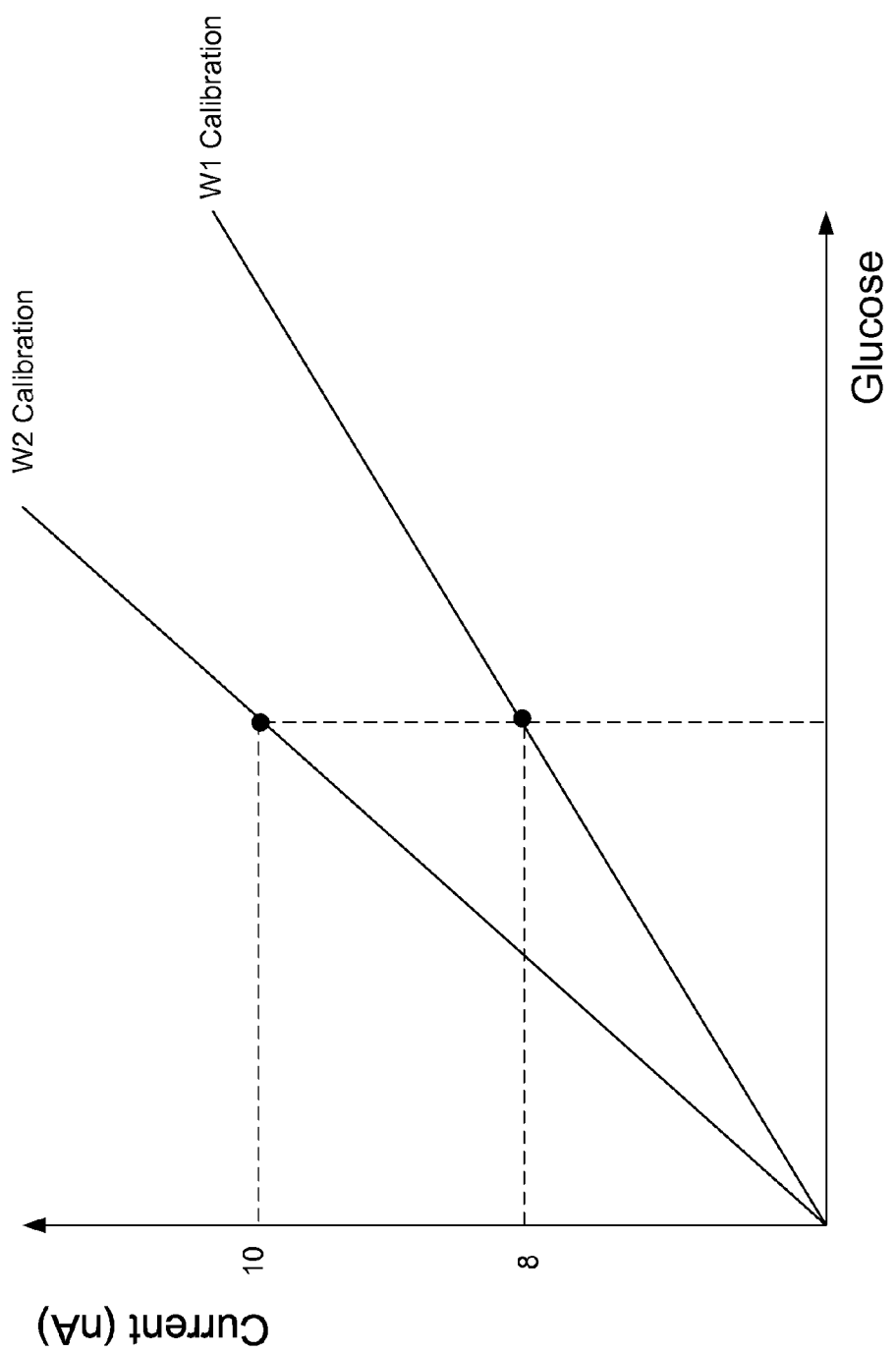
FIG. 6 illustrates a simulated graph of current flows at two working electrodes in accordance with a calibration, according to an embodiment of the invention.

In block 505, the first sensor is calibrated. As an initial part of the calibration process, the microcontroller or processing device may receive information associated with the detected sensor current at the first working electrode 414, and provide the received information to the receiving computer. To convert the received information regarding the detected current at the first working electrode 414 to an analyte measurement, the receiving computer utilizes a calibration function or curve. As an example, a calibration function or curve may be determined by receiving independent analyte measurements, which are correlated or transformed by the receiving computer to detected sensor current values. As an example, a patient in which the monitor or device has been embedded may take independent measures of glucose levels at one or more times (e.g., twice a day) using blood drop samples with a glucose strip/glucose meter. These independent measures of glucose levels are then input to the receiving computer such that the these independent measures of glucose levels can be mapped or correlated to the detected sensor current values. Based upon this mapping or correlation, the receiving computer can then generate a calibration function to convert future received information regarding the detected current at the first working electrode 414 to a glucose level measurement. As an example, FIG. 6 illustrates a calibration function or curve W1. It will be appreciated that the calibration function or curve may be updated or change over time when additional independent analyte measurements or other measurements of interest are provided to the receiving computer in association with detected sensor currents at the first working electrode 414. Indeed, the calibration function or curve may change over time due to degradation of sensor components or changes in the local environment.

In block 506, the microcontroller or processing device enables a second current measurement circuitry, perhaps when the first working electrode 414 is at or near the end of its useful life. According to an embodiment of the invention, the second current measurement circuitry is enabled by providing a biasing voltage or other power to the second transimpedance amplifier 408. Likewise, a working electrode set point (e.g., +600 mV relative to the reference electrode set point) is provided at the non-inverting input of the second transimpedance amplifier 408. In addition, in block 506, the microcontroller or processing device ruptures or displaces the reservoir cap for reservoir 417 to allow external environmental components (e.g., an analyte) to contact the second working electrode 418. It will be appreciated that the second transimpedance amplifier 408 and the second working electrode 418 may be enabled prior to rupturing or displacing the reservoir cap for reservoir 417 in order to verify that the reservoir 418 has remained sealed. Since the second working electrode 418 is coated with a biological recognition element, an electroactive product is generated near the second working electrode 418 based upon the presence of the appropriate analyte. The presence of the electroactive product near the second working electrode 418 results in a second sensor current being detected by the second current measurement circuitry (e.g., transimpedance amplifier 408 and sensing resistor R2) and provided at the output of the second transimpedance amplifier 408. The output of the second transimpedance amplifier 408 may be provided to the differential amplifier 428, which may provide information associated with the detected sensor current at the second working electrode 418 to the microcontroller or processing device.

At this point, the second sensor that includes the second working electrode 418 may optionally be calibrated when while the first control amplifier 402 is still operative. In this case, sensor currents may have been detected at the first working electrode 414 (e.g., first sensor currents) and the second working electrode 418 (e.g., second sensor currents) during operation of the first control amplifier 402. The comparison of the first sensor current and the second sensor current can be used to generate an initial calibration function or curve for the second sensor from the first sensor's calibration function or curve. As an example, several pairs of the sensor currents (I1, I2 for the first and second sensors) for the first and second working electrodes 414, 418 may be obtained for several concurrent periods of time when the control amplifier 402 is operative. Based upon a comparison of the sensor currents (instantaneous or averaged), the first sensor's calibration function can be scaled, offset, time shifted, transformed, or otherwise updated to generate the initial calibration function or curve for the second sensor. As an example, the scaling can be defined as a ratio or proportion such as, but not limited to, $$\frac{I2}{I1}.$$

As another example, an offset can be based upon I2−I1.

In block 508, the microcontroller or processing device disables the first control amplifier 402 and sets the second control amplifier 404 to an operative state after opening reservoir 419 to expose the second reference electrode 420. According to an embodiment of the invention, the second control amplifier 404 is set to an operative state by provide a biasing voltage or other power to the control amplifier 404. Likewise, a reference electrode set point (e.g., 0.5V) is provided at the non-inverting input of the second control amplifier 404. The first control amplifier 402 is disabled by turning off the first control amplifier 402, perhaps by eliminating a bias voltage for the first control amplifier 402. Thus, both the first working electrode 414 and the second working electrode 418 are now operative with the second reference electrode 420 operated by the second control amplifier 404. In this case, the microcontroller or processing device may receive information regarding the detected currents at the first working electrode 414 and the second electrode 418. Both the first working electrode 414 and the second working electrode 418 may operate simultaneously for a short period of time (e.g., a few hours, a day, etc.) so that the microcontroller or processing device may able to receive information regarding the detected sensor currents at the first working electrode 414 and the second electrode 418 for at least a few concurrent periods of time while the second control amplifier 404 is in operation.

In block 510, the second sensor associated with the second reference electrode 420 is calibrated. As a first part of the calibration process, the calibration function or curve for the first sensor, which was determined in conjunction with the operation of the first control amplifier 402, may now be verified with the operation of the second control amplifier 402. In particular, sensor currents may have been detected at the first working electrode 414 at one or more times prior to disabling the first control amplifier 402. Likewise, one or more sensor currents may have been detected at the first working electrode 414 at one or more times after enabling the second control amplifier 402. Next, the calibration function or curve for the first sensor may be scaled, offset, time shifted, transformed, or otherwise updated based upon a comparison of the sensor currents (e.g., for the first and second sensors) detected during operation of the first control amplifier 402 and the sensor currents (e.g., for the first and second sensors) detected during operation of second control amplifier 404. As an example, scaling may include multiplying the calibration function or curve by a ratio or proportion of sensor currents (I1, I2 for the first and second sensors) detected during operation of the first control amplifier 402 to the sensor currents (I1', I2' for the second sensors) detected during operation of second control amplifier 404. Example ratios or proportions can include but are not limited to the following:

$$\frac{I1'}{I1} \quad \text{(i)}$$

or $$\frac{I1' + I2'}{I1 + I2}. \quad \text{(ii)}$$

As another example, an offset may be determined by calculating a difference between sensor currents (I1, I2) detected during operation of the first control amplifier 402 to the sensor currents (I1', I2') detected during operation of second control amplifier 404. Example offsets can be based upon one or more of the following: (i) I1'−I1 or (iii) (I1'+I2')−(I1+I2).

As a second part of the calibration process, a calibration function or curve can be determined for the second sensor. According to an embodiment, the calibration is based upon a comparison of (i) the first sensor current (I1') detected by the first sensor (e.g., at first working electrode 414) and (ii) the second sensor current (I2') detected by the second sensor (e.g., at the second working electrode 418), where both the first and second sensor current are detected at one or more times when the second control amplifier 402 is in operation. The comparison of the first sensor current and the second sensor current will be used in block 510 to generate an initial calibration function or curve for the second sensor from the first sensor's calibration function or curve. As an example, several pairs of the sensor currents for the first and second working electrodes 414, 418 may be obtained for several concurrent periods of time. Based upon a comparison of the sensor currents, the first sensor's calibration function or can be scaled offset, time shifted, transformed, or otherwise updated to generate the initial calibration function or curve. At the simplest level, each calibration function can define a linear relationship between the measured current and the other value of interest (e.g., glucose concentration level), where the relationship is defined by a slope and an offset. Thus, the slope of the initial calibration function or curve W2 for the second sensor can be expressed as a percentage or ratio of the slope of the first sensor's calibration function or curve W1, where the percentage or ratio is determined by comparing the second sensor current and the first sensor current for the same value of interest (e.g., glucose concentration level). In the highly simplified example shown in FIG. 6, the slope of the initial calibration function W2 for the second sensor can be 10/8 (125%) the slope of the calibration function W1 for the first sensor. In block 510, once the calibration function or curve for the second sensor is determined, any measured second sensor current can be converted to another value of interest or analyte measurement.

As an example, as shown in FIG. 6, the first sensor current flowing at first working electrode 413 is detected as 8 nA while the second sensor current flowing at the second working electrode 418 is detected as 10 nA, for the same level of glucose concentration. In an embodiment, the second sensor current is higher than the first sensor current due to degradation of the biological recognition element layer of the first working electrode 514. The calibration function for the first sensor may convert the detected 8 nA to a particular glucose concentration level. Likewise, once a calibration function or curve has been derived for the second sensor, the 10 nA detected by the second sensor may likewise convert the detected 10 nA to approximately the same glucose level determined for the first sensor.

It will be appreciated that an alternative of the illustrative two-part calibration process above can be utilized where the initial calibration function or curve was previously determined during operation of the first control amplifier 402. In this case, sensor currents may have been detected at the first working electrode 414 at one or more times prior to disabling the first control amplifier 402. Likewise, one or more sensor currents may have been detected at the first working electrode 414 at one or more times after enabling the second control amplifier 402. Next, the initial calibration function or curve for the second sensor may be scaled, offset, time shifted, transformed, or otherwise updated based upon a comparison of the sensor currents (e.g., for the first and second sensors) detected during operation of the first control amplifier 402 and the sensor currents (e.g., for the first and second sensors) detected during operation of second control amplifier 404. As an example, scaling may include multiplying the calibration function or curve by a ratio or proportion of sensor currents (I1, I2 for the first and second sensors) detected during operation of the first control amplifier 402 to the sensor currents (I1', I2' for the second sensors) detected during operation of second control amplifier 404. Example ratios or proportions can include but are not limited to the following:

$$\frac{I2'}{I2} \quad (i)$$

or $$\frac{I1' + I2'}{I1 + I2}. \quad (ii)$$

As another example, an offset may be determined by calculating a difference between sensor currents (I1, I2) detected during operation of the first control amplifier 402 to the sensor currents (I1', I2') detected during operation of second control amplifier 404. Example offsets can be based upon one or more of the following: (i) I2'−I2 or (iii) (I1'+I2')−(I1+I2).

Following the calibration in block 510, processing proceeds to block 512. In block 512, the microcontroller or processing device disables the first current measurement circuitry. According to an embodiment of the invention, the microcontroller or processing device disables first current measurement circuitry by turning off the first transimpedance amplifier 408, perhaps by eliminating a bias voltage for the first transimpedance amplifier 408. Likewise, the microcontroller or processing device can disable the used working electrode 414, perhaps in accordance with techniques and components described in U.S. Patent Application Publication No. 2005/0096587 to Santini Jr. et al. Accordingly, the second working electrode 418 is now operative with the second reference electrode 420 and second control amplifier 404. It will be appreciated that calibration function or curve for the second sensor may be updated over time. For example, the calibration function or curve may be updated as additional independent analyte measures are provided to the receiving computer in association with detected currents at the second working electrode 418. Indeed, the calibration function or curve may change over time due to degradation of sensor components. It will further be appreciated that while the calibration has been described as being performed by the receiving computer, the calibration may also be performed, at least in part, by the microcontroller or processing device as well. For example, the microcontroller or processing device can scale the sensor currents as necessary when changing from a first sensor to a second sensor such that a scaled or converted value is transmitted from the microcontroller or processing device to the receiving computer.

It will be appreciated that variations of FIGS. 4A and 5 are available in accordance with embodiments of the invention. According to one variation, the opening of the reservoirs described in FIGS. 4A and 5 may differ if the electrodes are grouped in different configurations, as shown for example in FIGS. 4B and 4C. In addition, according to another variation, multiple sensors may be operative concurrently for an extended period of time. For example, two sensors can be operated in parallel for reliability. Likewise, for continuity, the operation of sensors may be staggered such that a first working electrode is one week old, a second working electrode is two weeks old, etc. In addition, instead of operating a single sensor, multiple sets of sensors may be operated together. As an example, a first set having two or more working electrodes may be operated, and a second set having two or more other working electrodes may be operated. The operations of the first and second sets of working electrodes may be also be staggered such that the first set is one week old, the second set is two weeks old, etc. Accordingly, while FIGS. 4A and 5 reference the operation of a single sensor, the operation could equally be applied to a set of sensors without departing from embodiments of the invention.

Figure 7:
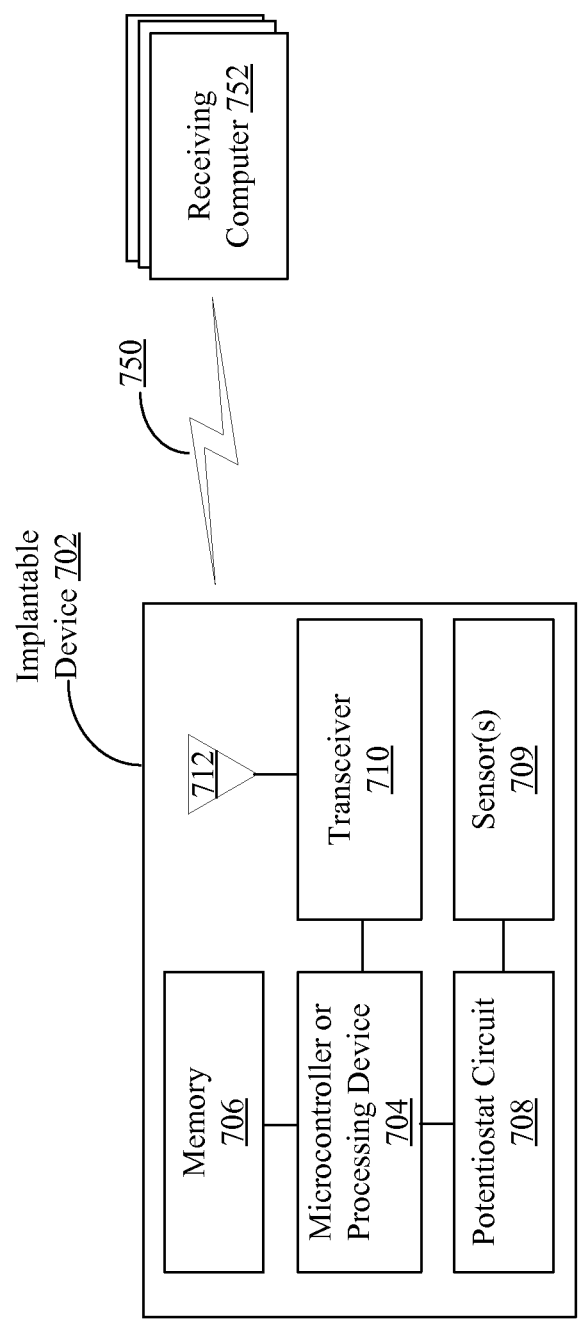
FIG. 7 illustrates an example embodiment of an implantable device, according to an embodiment of the invention.

FIG. 7 illustrates an example embodiment of an implantable device, according to an embodiment of the invention. As shown in FIG. 7, there is a illustrative implantable device 702. The implantable device can include a microcontroller or processing device 704 that is in communications with a memory 706, a potentiostat circuit 708, and a transceiver 710. The potentiostat circuit 708 can be implemented similar to those described in any of FIGS. 4A-4C, or variations thereof. In this regard, the potentiostat circuit 708 can include one or more amplifiers described herein. The potentiostat circuit 708 can also be connected to one or more sensors 709, which may include one or more electrodes described herein. The transceiver 710 can be coupled to an antenna 712. The memory 706 can include RAM, ROM, or any other storage device that stores information to support the processing of the microntroller or processing device 704, including information received from the potentiostat circuit 708 or utilized to control the potentiostat circuit 708. The memory 706 can also include computer-executable instructions, which when executed by the microcontroller or processing device 704, enable the microcontroller or processing device 704 to perform one or more of the steps or blocks described herein, including those described with respect to FIG. 5. In this regard, the implantable device 702 can communicate with a receiving computer 752 via a wireless network 750 to perform one or more of the steps or blocks described herein.

All documents cited in the Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Modifications and variations of the methods and devices described herein will be obvious to those skilled in the art from the foregoing detailed description. Such modifications and variations are intended to come within the scope of the appended claims.

That which is claimed:

1. A method for operating an array of biosensors, comprising:
    operating a first control amplifier that receives a first input from a first reference electrode and provides a first output to a counter electrode;
    enabling first current measurement circuitry for detecting at least one first current associated with a first working electrode while the first control amplifier is operative, wherein the counter electrode is operative with the first control amplifier to maintain a first specified voltage between the first reference electrode and the first working electrode;
    enabling second current measurement circuitry for detecting at least one second current associated with a second working electrode while the first control amplifier is operative, wherein the counter electrode is operative with the first control amplifier to maintain the first specified voltage between the first reference electrode and the second working electrode;
    disabling the first control amplifier subsequent to detecting the at least one second current associated with the second working electrode while the first control amplifier is operative;
    operating, subsequent to disabling the first control amplifier, a second control amplifier that receives a second input from a second reference electrode and provides a second output to the counter electrode, wherein the first current measurement circuitry detects at least one third current associated with the first working electrode while the second control amplifier is operative, wherein the second current measurement circuitry detects at least one fourth current associated with the second working electrode while the second control amplifier is operative, wherein the counter electrode is operative with the second control amplifier to maintain a second specified voltage between the second reference electrode and the second working electrode.

2. The method of claim 1, wherein a first sensor is associated with the first working electrode, and wherein a second sensor is associated with the second working electrode, further comprising:
    calibrating the second sensor by comparing the at least one third current to the at least one fourth current.

3. The method of claim 2, wherein the first sensor is associated with a first calibration function, wherein the first calibration function converts the at least one first current to a first value of interest, and wherein calibrating the second sensor comprising determining a second calibration function for the second sensor, wherein the calibration function converts the third working electrode current to a second value of interest, wherein the first value of interest and the second value of interest are substantially the same.

4. The method of claim 3, wherein a comparison of the at least one third current to the at least one fourth current is utilized to determine the second calibration function by scaling, offsetting, or time shifting the first calibration function for use as the second calibration function.

5. The method of claim 3, wherein the first calibration function is determined for the first sensor by correlating one or more values of the at least one first current to one or more corresponding analyte measurements obtained independently of the first sensor.

6. The method of claim 1, wherein the second current measurement circuitry is enabled when the first working electrode is near an end of its useful life.

7. The method of claim 1, wherein the first current measurement circuitry and the second measurement circuitry includes a respective transimpedance amplifier.

8. The method of claim 7, wherein the first current measurement circuitry and the second current measurement circuitry further includes a respective sensing resistor connected across an inverting input and an output of the respective transimpedance amplifier.

9. The method of claim 1, wherein at least one of the first working electrode and the second working electrode is coated with at least one layer of a biological recognition element.

10. The method of claim 9, wherein the biological recognition element, in the presence of an analyte, generates one or more electroactive active products or consumes one or more electroactive species, that induce current flow at the at least one of the first working electrode and the second working electrode.

11. The method of claim 10, wherein the biological recognition element is glucose oxidase, wherein the analyte is glucose, and wherein the generated electroactive product is hydrogen peroxide.

12. The method of claim 10, wherein the biological recognition element is glucose oxidase, wherein the analyte is glucose, and wherein the consumed electroactive species is oxygen.

13. The method of claim 1, wherein the first working electrode and the second working electrode are provided in respective reservoirs of a substrate.

14. The method of claim 13, wherein the respective reservoirs are sealed until the respective first and second working electrodes are to be utilized with the respective first current measurement circuitry or the second current measurement circuitry.

15. A method for operating an array of biosensors, comprising:
    enabling a first sensor that comprises a first working electrode, wherein a first control amplifier receives an input from a first reference electrode and provides a first output to a counter electrode, wherein the first control amplifier maintains a first specified voltage between the first reference electrode and the first working electrode, wherein at least one first current is detected at the first sensor while the first control amplifier is operative;
    prior to failure of the first sensor, enabling a second sensor that comprises a second working electrode, wherein the counter electrode is operative with the first control amplifier to maintain the first specified voltage between the first reference electrode and the second working electrode, wherein at least one second current is detected at the second sensor while the first control amplifier is operative;
    disabling the first control amplifier subsequent to detecting the at least one second current at the second sensor; and
    enabling, subsequent to disabling the first control amplifier, a second control amplifier that receives a second input from a second reference electrode and provides a second output to the counter electrode, wherein the counter electrode is operative with the second control amplifier to maintain a second specified voltage between the second reference electrode and the second working electrode, wherein at least one third current is detected at the first working electrode while the second control amplifier is operative, wherein at least one fourth current is detected at the second working electrode while the second control amplifier is operative.

16. The method of claim 15, wherein the first working electrode, the second working electrode, the first reference electrode, the second reference electrode, and the counter electrode are provided in a substrate, wherein the first control amplifier and the second control amplifier are provided in an integrated circuit, wherein the integrated circuit and the substrate is provided as part of an implantable device.

17. The method of claim 16, wherein the implantable device further includes a microcontroller for receiving the detected at least one first, second, third, and fourth current, wherein the microcontroller directs a wireless transmission of the detected at least one first, second, third, and fourth current to a receiving computer.

18. The method of claim 15, further comprising:
calibrating the second sensor by comparing (i) the at least one third current to the at least one fourth current, or (ii) the at least one first current to the at least one second current.

19. The method of claim 18, wherein a comparison of the at least one third current to the at least one fourth current, or the at least one first current to the at least one second current, is utilized to determine a second calibration function as a scaled version of a first calibration function, wherein the first calibration function is associated with the first sensor.

20. The method of claim 15, wherein at least one of the first working electrode and the second working electrode is coated with at least one layer of a biological recognition element.

21. The method of claim 15, wherein one or more sensing resistors are utilized in detecting one or more of the at least one first, second, third, and fourth current.

22. A device, comprising:
a plurality of control amplifiers, including at least a first control amplifier and a second control amplifier;
a plurality of current measurement circuitry, including at least first current measurement circuitry and second current measurement circuitry; and
a microcontroller in communication with the plurality of control amplifiers and the plurality of current measurement circuitry, wherein the microcontroller is configured to:
operate the first control amplifier that receives a first input from a first reference electrode and provides a first output to a counter electrode;
enable the first current measurement circuitry to detect at least one first current associated with a first working electrode while the first control amplifier is operative, wherein the counter electrode is operative with the first control amplifier to maintain a first specified voltage between the first reference electrode and the first working electrode;
enable the second current measurement circuitry to detect at least one second current associated with a second working electrode while the first control amplifier is operative, wherein the counter electrode is operative with the first control amplifier to maintain the first specified voltage between the first reference electrode and the second working electrode;
disable the first control amplifier subsequent to detecting the at least one second current associated with the second working electrode while the first control amplifier is operative;
operate, subsequent to disabling the first control amplifier, a second control amplifier that receives a second input from a second reference electrode and provides a second output to the counter electrode, wherein the first current measurement circuitry detects at least one third current associated with the first working electrode while the second control amplifier is operative, wherein the second current measurement circuitry detects at least one fourth current associated with the second working electrode while the second control amplifier is operative, wherein the counter electrode is operative with the second control amplifier to maintain a second specified voltage between the second reference electrode and the second working electrode.

23. The device of claim 22, wherein a first sensor is associated with the first working electrode, and wherein a second sensor is associated with the second working electrode, wherein the first sensor is associated with a first calibration function, wherein the first calibration function converts the at least one first current to a first value of interest, and the second sensor is calibrated to determine a second calibration function for the second sensor, wherein the calibration function converts the third working electrode current to a second value of interest, wherein the first value of interest and the second value of interest are substantially the same.

24. The device of claim 23, wherein the first calibration function is determined for the first sensor by correlating one or more values of the at least one first current to one or more corresponding analyte measurements obtained independently of the first sensor.

25. A sensor device, comprising:
a plurality of sensors, including at least a first sensor and a second sensor;
a plurality of control amplifiers, including at least a first control amplifier and a second control amplifier;
a microcontroller in communication with the plurality of sensors and the plurality of control amplifiers, wherein the microcontroller is configured to:
enable the first sensor that comprises a first working electrode, wherein the first control amplifier receives an input from a first reference electrode and provides a first output to a counter electrode, wherein the first control amplifier maintains a first specified voltage between the first reference electrode and the first working electrode, wherein at least one first current is detected at the first sensor while the first control amplifier is operative;
enable, prior to failure of the first sensor, a second sensor that comprises a second working electrode, wherein the counter electrode is operative with the first control amplifier to maintain the first specified voltage between the first reference electrode and the second working electrode, wherein at least one second current is detected at the second sensor while the first control amplifier is operative;
disable the first control amplifier subsequent to detecting the at least one second current associated with the second working electrode while the first control amplifier is operative; and
enable, subsequent to disabling the first control amplifier, the second control amplifier that receives a second input from a second reference electrode and provides a second output to the counter electrode, wherein the counter electrode is operative with the second control amplifier to maintain a second specified voltage between the second reference electrode and the second working electrode, wherein at least one third current is detected at the first working electrode while the second control amplifier is operative, wherein at least one fourth current is detected at the second working electrode while the second control amplifier is operative.

26. The sensor device of claim 25, wherein the second sensor is calibrated by comparing (i) the at least one third current to the at least one fourth current, or (ii) the at least one first current to the at least one second current.

27. The sensor device of claim 26, wherein a comparison of the at least one third current to the at least one fourth current, or the at least one first current to the at least one second current, is utilized to determine the second calibration function as a scaled version of a first calibration function, wherein the first calibration function is associated with the first sensor.

* * * * *